(12) United States Patent
Batista

(10) Patent No.: US 10,517,329 B2
(45) Date of Patent: Dec. 31, 2019

(54) SENSING IN AEROSOL GENERATING ARTICLES

(71) Applicant: PHILIP MORRIS PRODUCTS S.A., Neuchatel (CH)

(72) Inventor: Rui Batista, Morges (CH)

(73) Assignee: Philip Morris Products S.A., Neuchatel (CH)

(*) Notice: Subject to any disclaimer, the term of this patent is extended or adjusted under 35 U.S.C. 154(b) by 86 days.

(21) Appl. No.: 15/575,193

(22) PCT Filed: Jun. 9, 2016

(86) PCT No.: PCT/IB2016/053406
§ 371 (c)(1),
(2) Date: Nov. 17, 2017

(87) PCT Pub. No.: WO2016/199065
PCT Pub. Date: Dec. 15, 2016

(65) Prior Publication Data
US 2018/0146708 A1 May 31, 2018

(30) Foreign Application Priority Data
Jun. 12, 2015 (EP) .................................... 15171977

(51) Int. Cl.
*A24F 47/00* (2006.01)
*G01N 27/416* (2006.01)
*H05B 3/44* (2006.01)

(52) U.S. Cl.
CPC ......... *A24F 47/008* (2013.01); *G01N 27/416* (2013.01); *H05B 3/44* (2013.01)

(58) Field of Classification Search
CPC .................................................. A24F 47/008
See application file for complete search history.

(56) References Cited

U.S. PATENT DOCUMENTS 5,571,401 A 11/1996 Lewis et al.
8,449,824 B2 5/2013 Sun
(Continued)

FOREIGN PATENT DOCUMENTS

CN 103330274 A 10/2013
CN 103932406 A 7/2014
(Continued)

OTHER PUBLICATIONS

International Preliminary Report on Patentability issued for PCT/IB2016/053406, from the International Bureau of WIPO, Dec. 21, 2017; 6 pgs.
(Continued)

*Primary Examiner* — James Harvey
(74) *Attorney, Agent, or Firm* — Mueting, Raasch & Gebhardt, P.A.

(57) ABSTRACT

A smoking article includes a housing that has a mouthpiece and that is configured to receive an aerosol generating substrate. The smoking article also includes a sensor that is positioned at, for example, the mouthpiece and that is configured to detect an oronasal molecule of a prospective smoker of the article. The oronasal molecule can be a molecule that would be expected to be present in breath or saliva of a smoker but not in the breath or saliva of a non-smoker. The sensor is positioned to detect an amount or concentration of a molecule in the smoker's breath or saliva. The smoking article can use data transduced by the sensor to control delivery of an aerosol from the smoking article, such as to prevent delivery of the aerosol.

14 Claims, 3 Drawing Sheets

(56) References Cited

U.S. PATENT DOCUMENTS

| | | | |
|---|---|---|---|
| 2013/0220315 A1 | | 8/2013 | Conley et al. |
| 2015/0000683 A1 | * | 1/2015 | Liu |
| 2018/0140016 A1 | * | 5/2018 | Thorens ............... A24F 47/008 |
| 2018/0146708 A1 | * | 5/2018 | Batista ................ A24F 47/008 |
| 2019/0053538 A1 | * | 2/2019 | Batista ................ A24F 47/008 |

FOREIGN PATENT DOCUMENTS

| | | |
|---|---|---|
| EP | 1099102 B1 | 5/2008 |
| EP | 2654471 B1 | 7/2014 |
| RU | 2509516 C2 | 6/2011 |
| RU | 132318 U1 | 9/2013 |
| WO | WO 2008/139411 A2 | 11/2008 |
| WO | WO 2014/125483 A1 | 8/2014 |
| WO | WO 2014/159250 A1 | 10/2014 |
| WO | WO 2014/199233 A2 | 12/2014 |

OTHER PUBLICATIONS

European Extended Search Report from the European Patent Office, for EP 15171977.0, dated Dec. 18, 2015, 5 pgs.

International Search Report and Written Opinion for PCT/IB2016/053406, issued by the International Bureau of WIPO, dated Sep. 9, 2016; 9 pgs.

Russian Decision to Grant including the Search Report, issued by the Patent Office of the Russian Federation dated Aug. 30, 2019 for RU Application No. 2017134727; 16 pgs. Including English translation.

* cited by examiner

SENSING IN AEROSOL GENERATING ARTICLES

This application is the § 371 U.S. National Stage of International Application No. PCT/IB2016/053406, filed 9 Jun. 2016, which claims the benefit of European Application No. 15171977.0, filed 12 Jun. 2015.

FIELD OF INVENTION

This disclosure relates sensing in electronic aerosol generating devices.

BACKGROUND

Restriction of unauthorised access to nicotine-containing products, for example by non-adults, would be desirable for electronic smoking articles. A number of techniques have been proposed to prevent such unauthorised access. Examples of such techniques include fingerprint identification and unlocking with a mobile device, such as a mobile phone, after RFID check with an RFID reader installed on the mobile device. Such techniques are intended to limit the use of an electronic smoking article to a given individual, such as the individual with the distinctive fingerprint or the individual with the mobile device keyed to unlock the smoking article, or at least require the presence of the individual. Such techniques also require set up, such as storing of the fingerprint or keying of the mobile device, prior to initial use of the electronic smoking article.

It would be desirable to manufacture a smoking article that can reduce unauthorised use without requiring additional set up steps prior to initial use of the electronic smoking article. Advantages of examples of the present invention will be evident to those of skill in the art upon reading and understanding the present disclosure, which includes the claims that follow and the accompanying drawings.

SUMMARY

In one aspect of the present invention, a smoking article includes a housing that has a mouthpiece and that is configured to receive an aerosol generating substrate. The smoking article also includes a sensor that is for example positioned at the mouthpiece and that is configured to detect an oronasal molecule of a prospective smoker of the article. Preferably, the oronasal molecule is a molecule that would be expected to be present in breath or saliva of a smoker but not in the breath or saliva of a non-smoker. The sensor is positioned such that prior to a smoker placing their lips in contact with the mouthpiece or while a smoker's lips are placed in contact with the mouthpiece, the sensor can detect an amount or concentration of a molecule in the smoker's breath or saliva. The smoking article can store or report data regarding the amount of the oronasal molecule detected by the sensor to, for example, the smoker. In addition or alternatively, the smoking article can use data transduced by the sensor to control delivery of an aerosol from the smoking article, such as to prevent delivery of the aerosol.

Thus, examples of the invention can provide electronic smoking articles that include a sensor configured to detect an oronasal molecule, such as a molecule in a smoker's saliva or breath. Data from the sensor could be collected by the smoking article or could be used to control delivery of an aerosol from the smoking article.

Various aspects of the present invention may have one or more advantages relative to currently available or previously described electronic smoking articles. For example, some embodiments of electronic smoking articles described herein can allow for use of the article by smokers without having to set up the smoking article to prevent unintended access. By way of further example, some embodiments of the electronic smoking articles described herein can provide information to a smoker that can be physiologically relevant to the particular smoker, such as the amount or concentration of an oronasal molecule associated with smoking. The smoker can then track changes in the amount or concentration of the oronasal molecule over time. Such tracking may be helpful to smokers in, for example, smoking cessation programs. These and other advantages of various aspects of the present invention will be evident to those of skill in the art upon reading and understanding the present disclosure.

The present invention is applicable to any suitable smoking article. Any smoking article that includes a mouthpiece configured to contact a smoker's lips or to be placed in proximity to a smoker's mouth can be used or modified in accordance with the present invention. As used herein, a "smoking article" is an article that is configured to deliver an aerosol to a smoker using the article. For purposes of the present invention, the smoking article includes a one-part or multiple-part housing that has a mouthpiece and that is configured to receive an aerosol generating substrate, such as a nicotine-containing aerosol generating substrate. The substrate can be in any suitable form. For example, the substrate can include tobacco. In some embodiments, the substrate includes a liquid composition comprising nicotine. In some embodiments, the substrate comprises a dry powder containing nicotine, such as a nicotine salt. A "smoking article" includes articles that heat, directly or indirectly, the aerosol generating substrate to produce the aerosol and articles that do not heat the substrate but rather use air flow or a chemical reaction to deliver aerosol.

As used herein, an "electronic smoking article" is a smoking article that has one or more electrical components. Preferably, at least some of the one or more electrical components control delivery of an aerosol from the substrate to the smoker via the mouthpiece. The electrical components can include a substrate heater, which can include, for example, one or more electrically resistive elements or can include an electrically controllable valve positioned and configured to allow or prevent passage of an aerosol generated from the substrate to a smoker via the mouthpiece. Control of a heater, a valve or other electrical component can be accomplished by control electronics. Control electronics can be provided in any suitable form and may, for example, include a controller or a memory and a controller. The controller can include one or more of an Application Specific Integrated Circuit (ASIC) state machine, a digital signal processor, a gate array, a microprocessor, or equivalent discrete or integrated logic circuitry. Control electronics can include memory that contains instructions that cause one or more components of the control electronics to carry out a function or aspect of the control electronics. Functions attributable to control electronics in this disclosure can be embodied as one or more of software, firmware, and hardware.

It will be appreciated that a smoking article that does not include control electronics can be readily modified to incorporate control electronics, such as a controllable valve, to carry out one or more embodiments of the present invention.

Regardless of the type of electronic smoking article, an oronasal molecule sensor can be placed relative to the mouthpiece such that placement of a smoker's lips on the mouthpiece will transfer saliva to the sensor so that the sensor can detect the molecule in the saliva. In addition or alternatively, an oronasal molecule sensor can be placed relative to the mouthpiece such that placement of the mouthpiece in proximity to a prospective smoker's mouth will transfer the prospective smoker's breath to the sensor so that the sensor can detect the molecule in the breath.

Preferably, the sensors are capable of detecting very low concentrations of oronasal molecules that, in some cases, can provide for detection of oronasal molecules at extended distances, such as 100 millimetres to 150 millimetres.

Any one or more sensors may be positioned at or in proximity to the mouthpiece and can be configured to detect any one or more oronasal molecules in saliva, breath or saliva and breath. Preferably, at least one oronasal molecule detected by a sensor is a molecule that can be detected from a person's breath. Preferably at least one oronasal molecule detected by a sensor is a molecule that would be expected to be present in higher concentrations in smokers than in non-smokers. Examples of oronasal molecules that would be expected to be present in higher concentrations in smokers include carbon monoxide, acetone, nitric oxide, nitric oxide factors such as FeNO, nitric oxide synthases, endothelin-1 (ET-1), preproendothelin-1 (PPET1); formaldehyde; acetaldehyde; hydrogen cyanide; methylundecane; methylpentadecane; and methylpropane. Many of these compounds listed above can be present in the breath of smokers for many weeks or months after the last smoking experience at levels higher than in the breath of non-smokers. Molecules that can be detected to differential between adults and non-adults include isoprene molecules, related derivates of isoprene molecules, and specific derivates of alkanes and methylalkanes.

Preferably, a sensor is configured to detect an amount of an oronasal molecule within a relevant range of concentrations. Detection of any amount of a molecule that would be expected to be present in breath or saliva of a smoker but not a non-smoker would be sufficient to distinguish between a smoker and a non-smoker. However, some molecules may be present in breath or saliva of both smokers and non-smokers. In such cases, a sensors ability to detect concentrations of the molecule within a range that is relevant to distinguish between a smoker and a non-smoker can be important.

An electronic smoking article of the present invention can employ any suitable sensor configured to detect an oronasal molecule. Preferably, an oronasal molecule sensor is an electrochemical sensor. Any suitable electrochemical sensor can be employed. Preferably, the sensor includes an oronasal molecule-sensitive coating disposed on a transducer, where selective binding of the oronasal molecule to the coating is translated a signal or change in signal by the transducer. For example, binding of the oronasal molecule can result in a change in frequency, current or voltage, which can be correlated to an amount of the oronasal molecule present in saliva or breath of a smoker. In some embodiments, mass change of the coating results in changes in resonance frequency of the transducer, which translates into a proportional electrical signal. For purposes of the present invention, a "coating," as it relates to a sensor, is a coating, layer, or film.

Preferably, an oronasal sensor for use in a smoking article of the present invention is a RFID tag sensor that includes a RFID tag and an oronasal molecule-sensitive coating operably coupled to the RFID tag. RFID sensors can advantageously be passive, requiring no battery power to be used by the sensor. An RFID sensor can be interrogated by a powered RFID reader as known in the art. In many embodiments, a resonance frequency of the RFID sensor changes as differing amounts of an oronasal molecule bind to the coating. The RFID reader can sweep the sensor to determine the resonance frequency of the tag, which can correlate to the amount of oronasal molecule present. The RFID reader can, in some embodiments, be configured to interrogate the RFID tag of the sensor at only one resonance frequency, such as the resonance frequency of the sensor without bound analyte or the frequency of the sensor with bound analyte.

In some embodiments, binding of an oronasal molecule to a coating of an RFID sensor can cause a portion of an antenna of the RFID sensor to open, such as to cut open or to be suppressed, which can modify the resonance frequency of the RFID tag to indicate presence of the oronasal molecule.

Any suitable coating or layer can be disposed on a transducer, such an RFID tag or printed circuit board, for detecting a relevant oronasal molecule. For example, selective detection of nitric oxide molecules (eNO) and factors (FE NO) or synthases (NOS), can be done using specific sequence of oligonucleotides which may include different divalent cations, including $Ni^{2+}$, $CO_2$, $Mg^{2+}$, and $Mn^{2+}$, adsorbed to an array of semiconducting single-walled carbon nanotubes. In general, carbon nanotubes impregnated or wrapped with specific materials or molecules can detect the targeted molecules, which then change the properties of the carbon. For example, the carbon can be a chemiresistive material based on carbon nanotubes (CNTs) wrapped with a calixarene-substituted polythiophene, which displays a selective and sensitive response to xylene by conductance changes. Similar host-guest chemistry selection of mercury cadmium telluride (HgCdTe) can be used for detection of isoprene molecules or related derivates of isoprene molecules, and specific derivates of alkanes and methylalkanes. Carbon monoxide can be detected by host-guest chemistry using porphyrin molecules in carbon based hosts, such as carbon nanotubes or graphene structures. Doped tin dioxide ($SnO_2$) or tungsten trioxide ($WO_3$) sensors (including Ag, Pd, Cu, Pt, PtAg) can be used to detect other molecules that are present in smokers breath, such as formaldehyde, acetaldehyde, hydrogen cyanide, methylundecane, methylpentadecane, and methylpropane. For $CO_2$ detection, clad-etched Fiber Bragg Grating with polyallylamine-amino-carbon CNTs coated on the surface of the core can be used to achieve level of sensitive detection of about 75 ppm. Preferably, an oronasal detection system of the present invention is re-usable if the mouthpiece is re-usable. If the mouthpiece is configured to be disposed after a single use, the oronasal detection system can also be configured for one-time use. Regardless of the oronasal molecule detected, nicotine metabolite data obtained by a smoking article of the present invention can be used for any one or more suitable purpose, only a few of which are described in the present disclosure in more detail.

In preferred embodiments, a smoking article includes an oronasal molecule sensor operably coupled to memory, such as RAM, to store data obtained from the sensor. Memory can be operably coupled to appropriate computing apparatus to analyse the sensor data to, for example, analyse whether the data is indicative of the presence or a particular amount of the oronasal molecule. The computing apparatus can be operably coupled to a display to display information relating to the sensed data. In some embodiments, the smoking article includes a display. In addition or alternatively, the smoking article can include output apparatus to transfer stored sensor data to another device for display, analysis or display and analysis. Output apparatus can include output communication apparatus. Output communication apparatus can be wired or wireless communication apparatus. Wired output communication apparatus can include one or more ports, such as a USB port or a fire wire port, for operably coupling the smoking article to another computing apparatus, such as a smart phone or a computer. Wireless communication apparatus include telemetry, Bluetooth, infrared, or other wireless transmitters for operably coupling the smoking article to another computing apparatus, such as a smart mobile phone or a computer. The computer, smart mobile phone, or other computing apparatus can be used to receive data obtained from a sensor. The computing apparatus can then be used to analyse, display, or analyse and display the sensed data.

Information regarding the presence or amount of an oronasal molecule can be advantageously used by a smoker on a smoking cessation program or a smoker in a process from switching from smoking combustible smoking articles such as cigarettes to smoking electronic cigarettes. For example, if the oronasal molecule is a molecule expected to be in higher concentrations in smokers than in non-smokers, the molecule may be a good candidate to monitor to allow a smoker to track progress in a smoking cessation program. If the oronasal molecule is a molecule expected to be in higher concentrations in smokers of combustible smoking articles than in smokers of non-combustible electronic smoking articles, the molecule may be a good candidate to monitor to allow a smoker to track progress in a combustible smoking article cessation program.

In preferred embodiments, a smoking article includes an oronasal molecule sensor operably coupled to control electronics configured to control delivery of an aerosol from the smoking article. Preferably, the control electronics are configured to control delivery of the aerosol based on data received from the sensor. In some embodiments, the control electronics are configured to prevent the article from delivering an aerosol from the article based on data received from the sensor. For example, if the oronasal molecule detectable by a sensor is a molecule expected to be present in higher concentrations in smokers than in non-smokers and if a concentration or amount of the oronasal molecule is below a predetermined minimum threshold, the control electronics may at least partially prevent delivery of the aerosol from the device. In such embodiments, accidental or unwanted use of the smoking article can be prevented. By way of example, the device can be configured to prevent non-smokers from effectively using the smoking article or from receiving a dose, or a full dose, of the aerosol. Because non-smokers should have lower levels of a molecule indicative of smoking in their breath or saliva, the amount of the molecule detected by the sensor should be below the predetermined minimum threshold when the non-smoker attempts to use the smoking article. If the minimum threshold is not met, control electronics of the device can at least partially prevent aerosol from being delivered by the smoking article. The amount aerosol prevented from being delivered may be any portion of a full dose that the smoking article is configured to deliver. Preferably, the amount of nicotine prevented from being delivered is the full dose.

In some embodiments where the smoking article is configured to prevent delivery of an aerosol, the smoking article includes a controllable valve operably coupled to an oronasal molecule sensor. The valve can be positioned along a flow path that extends from the aerosol generating substrate to a mouth end of the mouthpiece. The valve can be configured to adapt default a configuration, such as closed, to prevent delivery of aerosol to a smoker through the mouthpiece unless the minimum threshold is met. Alternatively, the valve can be configured to adapt a default configuration, such as open, to allow delivery of aerosol to a smoker through the mouthpiece, and if a concentration or amount of an oronasal molecule is below the minimum threshold, the valve can adapt a configured to prevent delivery of the aerosol.

In some embodiments where the smoking article is configured to prevent delivery of an aerosol, the smoking article includes a heater configured to heat a substrate to generate an aerosol to be delivered to a smoker. The heater can be operably coupled to an oronasal molecule sensor. The heater may be prevented from being activated unless a concentration or amount of a nicotine metabolite is detected by the sensor as being above the predetermined minimum threshold. Alternatively, the heater may be configured to adapt a default configuration of being activated, and if a concentration or amount of an oronasal molecule is below the minimum threshold, the heater can be inactivated. In such cases, some amount of aerosol may be available for delivery to smoker due to prior heating of the substrate.

In some embodiments, a smoking article includes a heater configured to heat a substrate to generate an aerosol to be delivered to a smoker and includes a controllable valve, such as a valve as discussed above.

Alternatively or in addition to preventing an amount of aerosol from being delivered from the smoking article, control electronics of the smoking article can be operably coupled to alarm apparatus to provide an alert that a minimum threshold is not met. Alarm apparatus may include, for example, apparatus that when activated cause the smoking article to vibrate, a speaker to provide an audible sound, led lights that can flash, and a display for presenting a warning. Alternatively, the alarm apparatus can be external to the smoking article and coupled to output apparatus of the smoking article. Alarm apparatus can include, for example, a smart mobile phone.

It will be understood that the preferred embodiments described herein can be combined in any suitable matter. For example, a smoking device configured to prevent delivery of an aerosol when a minimum threshold is not met can also be configured to one or more of store, display and output information regarding data obtained by a nicotine metabolite sensor.

In some embodiments, a smoking article having an oronasal sensor according to the present invention also includes one or more components configured to receive data from an oronasal sensor. For example, if the sensor includes an RFID tag, the smoking article can include an RFID reader. The RFID reader can be positioned at any suitable location of the smoking article. Preferably, the RFID reader is positioned on or in a reusable portion of the smoking article. The RFID tag sensor is positioned at the mouthpiece, which can be disposable or reusable, depending on the configuration of the electronic smoking article.

An electronic smoking article according to some preferred embodiments of the present invention can include an RFID reader configured to detect the identity of a substrate inserted into the article if the substrate or a container housing the substrate includes an RFID tag. The data from the reader regarding the tag can be sent to control electronics to determine the identity of the substrate based on the tag by, for example, reference to a look up table. The control electronics can be configured to control the delivery of an aerosol from the substrate based on the identity of the substrate. For example, if the substrate is determined to not contain nicotine, the lock out features described above, such as detection of an oronasal molecule at levels below a threshold, can be disabled to allow smoking of the aerosol regardless of whether the user is determined to be a smoker or a non-smoker.

In some embodiments, an electronic smoking article of the present invention includes one or more components that cause sensor detection components to be activated when an aerosol generating substrate or container housing the substrate is received by the housing of the electronic smoking article. For example, the smoking article may include a switch that is positioned and actuated when the substrate or container is received by the housing. Actuation of the switch can cause the one or more sensor detection components to be activated. Such activation of the detection components can serve to save power, such as battery power, by not causing power to be diverted to the detection components when not needed. In some embodiments, the one or more detection components are deactivated after a certain period of time even of the substrate or container are not removed from the housing.

In some embodiments, an electronic smoking article of the present invention includes one or more components that cause sensor detection components to be activated an oronasal molecule is detected, allowing power to be automatically switching ON based on specific molecule detection within proximity range of the mouth or nose of a smoker. The device can also be configured to automatically switch ON the power for stand-by mode of another component in the device, such as a puff detection sensor.

While electronic smoking articles that already include on-board electronics are described in detail in this disclosure, it will be understood that non-electronic smoking articles can include a sensor as described herein. For example, an RFID tag sensor can be positioned at or in proximity to a mouthpiece of a non-electronic smoking article and a separate device having an RFID reader can be used to determine the presence or concentration of the oronasal molecule detected by the RFID tag sensor.

All scientific and technical terms used herein have meanings commonly used in the art unless otherwise specified. The definitions provided herein are to facilitate understanding of certain terms used frequently herein.

As used herein, the singular forms "a", "an", and "the" encompass embodiments having plural referents, unless the content clearly dictates otherwise.

As used herein, "or" is generally employed in its sense including "and/or" unless the content clearly dictates otherwise. The term "and/or" means one or all of the listed elements or a combination of any two or more of the listed elements.

As used herein, "have", "having", "include", "including", "comprise", "comprising" or the like are used in their open ended sense, and generally mean "including, but not limited to". It will be understood that "consisting essentially of", "consisting of", and the like are subsumed in "comprising," and the like.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure, including the claims.

BRIEF DESCRIPTION OF THE DRAWINGS

Referring now to the drawings, in which some aspects of the present invention are illustrated. It will be understood that other aspects not depicted in the drawings fall within the scope and spirit of the present invention. The drawings are schematic drawings and are not necessarily to scale. Like numbers used in the figures refer to like components, steps and the like. However, it will be understood that the use of a number to refer to a component in a given figure is not intended to limit the component in another figure labelled with the same number. In addition, the use of different numbers to refer to components in different figures is not intended to indicate that the different numbered components cannot be the same or similar to other numbered components.

DETAILED DESCRIPTION

Figure 1:
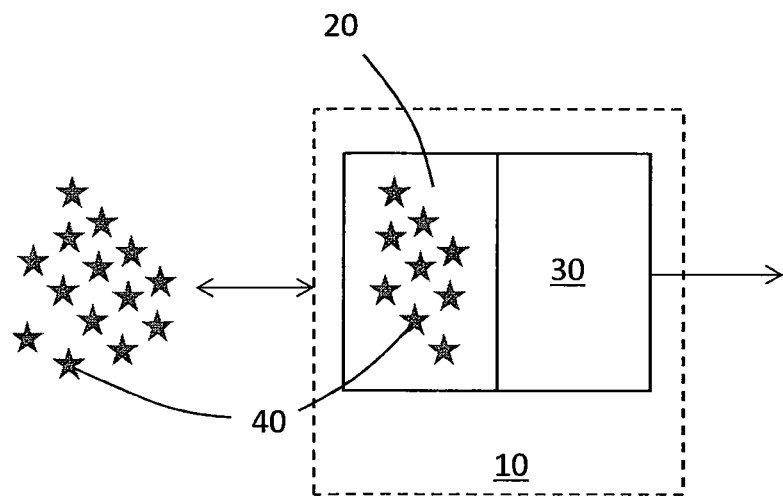
FIG. 1 is a schematic diagram depicting an oronasal molecule electrochemical sensor and scheme for transducing a signal related to an amount or concentration of the oronasal molecule detected by the sensor.

Referring now to FIG. 1, an electrochemical oronasal sensor 10 in accordance with various embodiments of the present invention can include a transducer 30 and a coating 20 or layer disposed on the transducer. The coating 20 specifically or selectively interacts with an oronasal molecule 40 via, for example, a physiochemical reaction. The transducer 30 outputs a signal based on, for example, the mass of the metabolite 40 present in the coating 20. In embodiments, the signal output is a signal in response to an interrogation. The transducer 30 can be an RFID tag.

Figure 2:
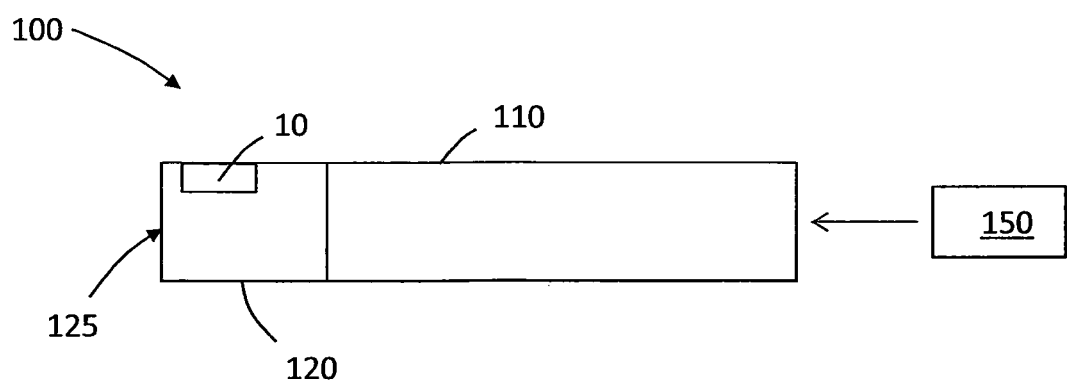
FIGS. 2-3 are schematic diagrams side views of a smoking article according to various embodiments of the present invention.

Referring now to FIG. 2, a smoking article 100 in accordance with various embodiments of the present invention includes a housing 110 that has a mouthpiece 120 and is configured to receive an aerosol generating substrate 150. The mouthpiece 120 defines a mouth end 125. An oronasal molecule sensor 10 is positioned along the mouthpiece such that when a smoker places their lips against the mouthpiece or when the mouthpiece is placed in proximity to a smoker's mouth, the sensor 10 can detect an amount or concentration of nicotine metabolite in the smoker's saliva or breath. The housing 110 may be formed of a single piece or multiple interconnected pieces. The housing 110 may be configured to receive the substrate 150 at any suitable location. One or more electrical components (not shown in FIG. 2) can be disposed in the housing 110.

Figure 3:
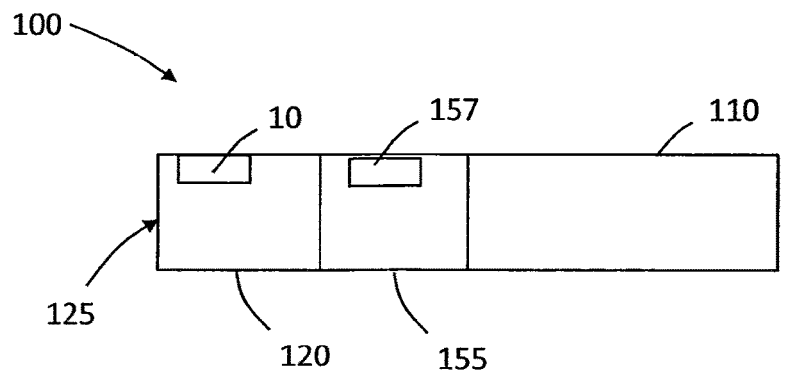

Referring now to FIG. 3, a smoking article 100 in accordance with various embodiments of the present invention includes a housing 110 that has a mouthpiece 120 and is configured to receive a container 155 containing an aerosol generating substrate. The container 155 forms part of a multi-part housing 110. The mouthpiece 120 defines a mouth end 125. An oronasal molecule sensor 10 is positioned along the mouthpiece such that when a smoker places their lips against the mouthpiece or when the mouthpiece is placed in proximity to a smoker's mouth, the sensor 10 can detect an amount or concentration of nicotine metabolite in the smoker's saliva or breath. The container 155 includes an RFID tag 157 to provide identity of the substrate within the container. One or more electrical components (not shown in FIG. 2) can be disposed in the housing 110.

Figure 4:
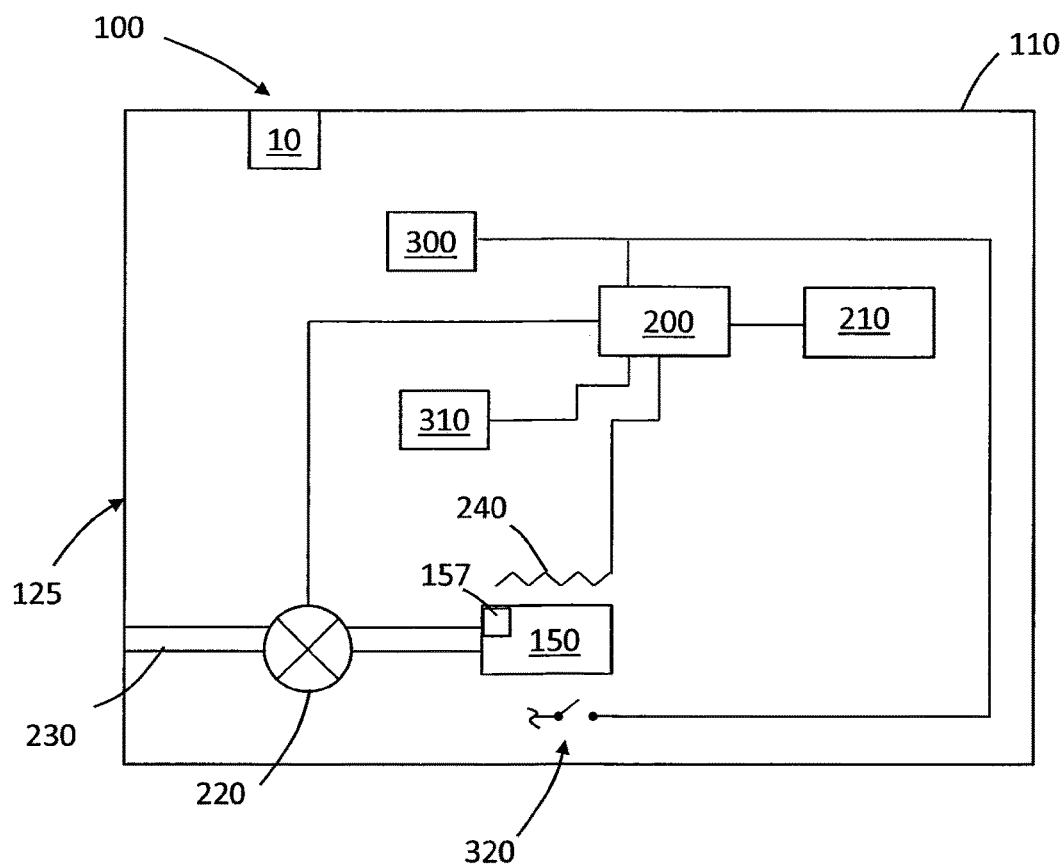
FIG. 4 is a schematic diagram illustrating some components of a smoking article according to various embodiments of the present invention.

Referring now to FIG. 4, a smoking article 100 in accordance with various aspects of the present invention includes a housing 110 configured to receive an aerosol generating substrate 150. The housing 110 includes a mouth end 125. An oronasal molecule sensor 10, which is an RFID sensor in the depicted embodiment, is positioned in proximity to the mouth end 125. Electrical components are stored in the housing 110. The smoking article 100 includes a power source 210 operably coupled to control electronics 200. Power source 210 can be any suitable power source, such as a battery, a capacitor, or the like. Preferably, the power source 210 is a rechargeable battery, such as a rechargeable lithium ion battery, a rechargeable nickel-cadmium battery, or the like.

In the embodiment depicted in FIG. 4, the control electronics 200 are operably coupled to sensor 10 via RFID reader 300. Control electronics 200 are also operably coupled to valve 220 and heater 240 in the depicted embodiment. Valve 220 is positioned along a pathway 230 that extends from substrate 150 to mouth end 125 through which aerosol generated by substrate can be transported. Valve 220 can adapt an open or closed configuration to allow or prevent the aerosol from traveling from substrate 150 to mouth end 125. Valve 220 can be controlled by control electronics 200 which can instruct valve whether to adapt the open or closed configuration based on data received from sensor 10.

Heater 240 is positioned in contact with or in proximity to substrate 150 and is configured to heat substrate to cause an aerosol to be generated by the substrate 150. Heater 240 can be controlled by control electronics 200 so that the extent of heating of the substrate 150 can be controlled based on data received from sensor 10.

In the embodiment depicted in FIG. 4, the smoking article 100 includes a second RFID reader 310 configured to interrogate and determine the resonance frequency of RFID tag 157 disposed on substrate 150 or a container housing the substrate. In some embodiments, one RFID reader 300, 310 can read both RFID tag of sensor 10 and RFID tag 157 of substrate 150.

The depicted electronic smoking article 100 also includes a switch 320 that is actuated by receipt of the substrate 150 or container housing the substrate by the housing 110. The switch 320, when actuated, can activate RFID reader 300.

Figure 5:
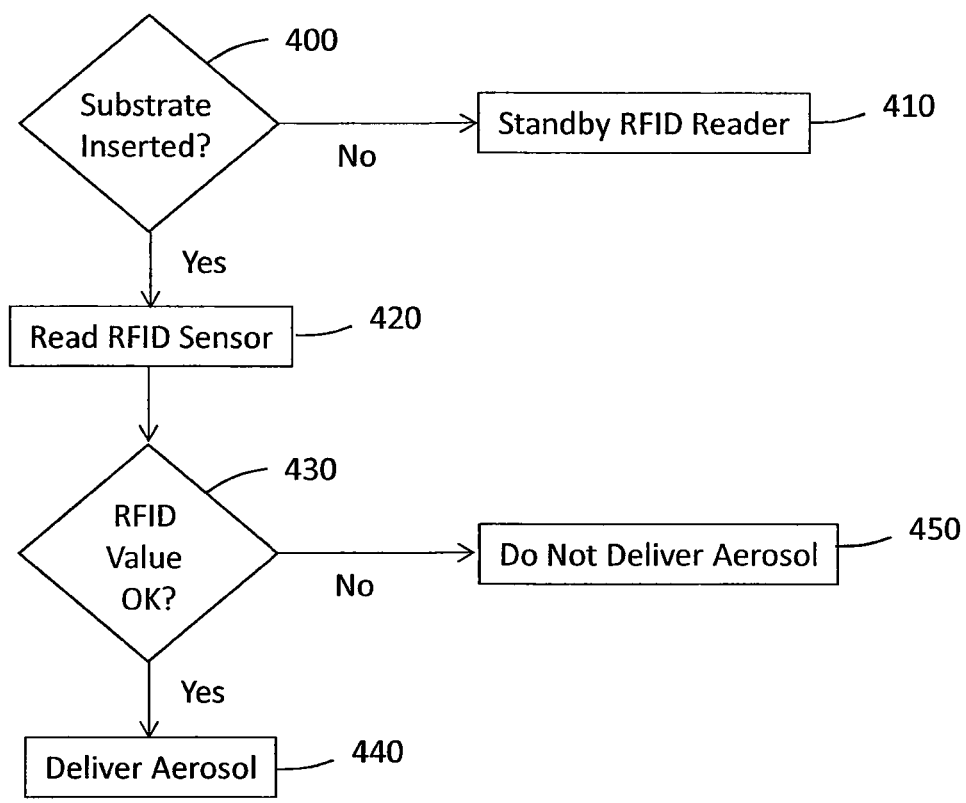
FIG. 5 is a flow chart illustrating aspects of a process that can be carried out by a smoking article in accordance with various aspects of the present invention.

Referring now to FIG. 5, a flow diagram is shown illustrating a process that can be carried out by a smoking article or system according to various embodiments of the present invention. At step 400, a determination is made as to whether a substrate is inserted into the smoking article. This can be determined by, for example, determining whether switch 320 as depicted in FIG. 4 is actuated. If the substrate is not inserted, one or more sensor reading components, such as, for example, RFID reader 300 as depicted in FIG. 4, remains on standby (410). If the substrate is inserted, the one or more sensor reading components are activated to read the RFID sensor (420), such as RFID sensor 10 as depicted in FIG. 4. A determination is then made as to whether the value obtained by the RFID sensor is appropriate (430) for delivering aerosol (440) from the smoking article. If the RFID value is not appropriate, the aerosol is not delivered (450).

Determination (430) can be made by, for example, control electronics 200 as depicted in FIG. 4. If appropriate, control electronics can, for example, activate a heater (such as heater 240 depicted in FIG. 4), activate a valve (such as valve 220 depicted in FIG. 4), or activate a heater and a valve to allow an aerosol from a substrate (such as substrate 150 depicted in FIG. 4) to be delivered to a smoker (such as through pathway 230 as depicted in FIG. 4).

Thus, methods, systems, devices, compounds and compositions for SENSING IN AEROSOL GENERATING ARTICLES are described. Various modifications and variations of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are apparent to those skilled in electronic smoking article manufacturing or related fields are intended to be within the scope of the following claims.

The invention claimed is:

1. A smoking article comprising:
a housing having a mouthpiece and configured to receive an aerosol generating substrate;
a sensor positioned at or in proximity to the mouthpiece and configured to detect an oronasal molecule of a prospective smoker of the article; and
control electronics configured to control delivery of an aerosol generated from the aerosol generating substrate through the mouthpiece, wherein the control electronics are operably coupled to the sensor and are configured control the delivery of the amount of the aerosol based on data received from the sensor.

2. The smoking article of claim 1, further comprising memory operably coupled to the sensor and configured to store data received from the sensor.

3. The smoking article of claim 1, wherein the control electronics are further configured to identify the aerosol generating substrate received by the housing and wherein the control electronics are further configured to control the delivery of the aerosol based on the identity of the substrate.

4. The smoking article of claim 1, further comprising a heater positioned and configured to heat the aerosol generating substrate to produce the aerosol.

5. The smoking article of claim 4, wherein the heater is operably coupled to the control electronics and wherein the control electronics are configured to control the extent to which the heater heats the substrate to control the amount of aerosol generated.

6. The smoking article of claim 1, wherein the control electronics include a controllable valve positioned along a flow path between a mouth end of the mouthpiece and the aerosol generating substrate, wherein the valve is configured to adapt a configuration that allows flow of the aerosol from the substrate to the mouth end of the mouth piece and to adapt a configuration that prevents flow of the aerosol from the substrate to the mouth end of the mouth piece.

7. The smoking article of claim 1, wherein the control electronics are configured to at least partially prevent delivery the aerosol if data received from the sensor is indicative of the prospective smoker being a non-smoker.

8. The smoking article of claim 1, wherein receipt of the aerosol generating substrate by the housing causes activation of one or more components of the control electronics that are configured to receive data from the sensor.

9. The smoking article of claim 8, further comprising a switch positioned and configured to be actuated when the substrate is received by the housing, and wherein actuation of the switch causes the one or more components of the control electronics that are configured to receive data from the sensor.

10. The smoking article of claim 1, wherein the sensor comprises an RFID tag and a coating sensitive to the oronasal molecule disposed on the RFID tag.

11. The smoking article of claim 10, wherein binding of the oronasal molecule to the coating causes a shift in output frequency of the RFID tag.

12. The smoking article of claim 1, wherein the sensor is configured to detect one or more of carbon monoxide, acetone, nitric oxide, nitric oxide factors, nitric oxide synthases, endothelin-1, preproendothelin-1, formaldehyde, acetaldehyde, hydrogen cyanide, methyundecane, methylpentadecane, and methylpropane.

13. The smoking article of claim 1, and the nicotine-containing aerosol generating substrate.

14. The smoking article of claim 13, wherein the substrate comprises one or more of a nicotine-containing liquid composition and a nicotine-containing dry powder.

* * * * *